United States Patent [19]

Muto

[11] Patent Number: 4,552,558
[45] Date of Patent: Nov. 12, 1985

[54] PRESSURE WARNING, INDICATING AND APPLYING MONITOR FOR CUFF TYPE INDWELLING DEVICES

[76] Inventor: Rudolph Muto, 24 Williams St., Andover, Mass. 01810

[21] Appl. No.: 513,645

[22] Filed: Jul. 14, 1983

[51] Int. Cl.⁴ ............................................. A61M 25/00
[52] U.S. Cl. ............................... 604/100; 116/DIG. 8
[58] Field of Search ................................. 604/96–103; 116/D8, D9; 79/748; 128/344, 207.15

[56] References Cited

U.S. PATENT DOCUMENTS 3,602,226  8/1971  Ericson ................................. 604/98
4,507,116  3/1985  Liebinsohn ........................... 604/99

Primary Examiner—C. Fred Rosenbaum
Assistant Examiner—Karen Kaechele
Attorney, Agent, or Firm—Pearson & Pearson

[57] ABSTRACT

A cuff type indwelling device such as a tracheal tube, catheter or the like is provided with a cuff balloon and a pilot balloon of full volume non-stretchable, non-resilient flexible material, and means for inflating both balloons. The pilot balloon is of generally spherical shape when expanded and is enclosed in a longer pressure monitoring balloon of resilient stretchable material. As the drum shaped pilot balloon progressively increases in diameter, during application of pressure, it progressively changes the configuration of the pressure monitoring balloon from elongated cylindrical shape, to oval shape, to substantially spherical shape, thereby visually indicating to the surgeon low side cuff pressure, medium cuff pressure, and high side cuff pressure.

9 Claims, 7 Drawing Figures

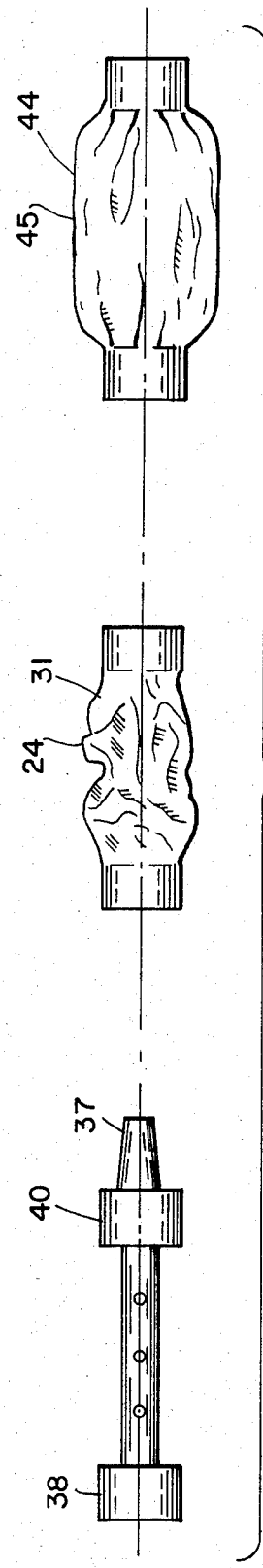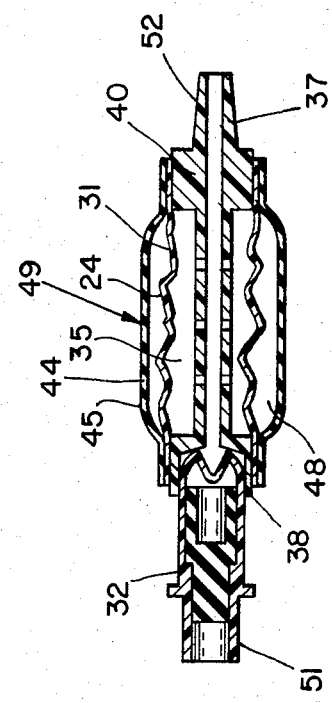

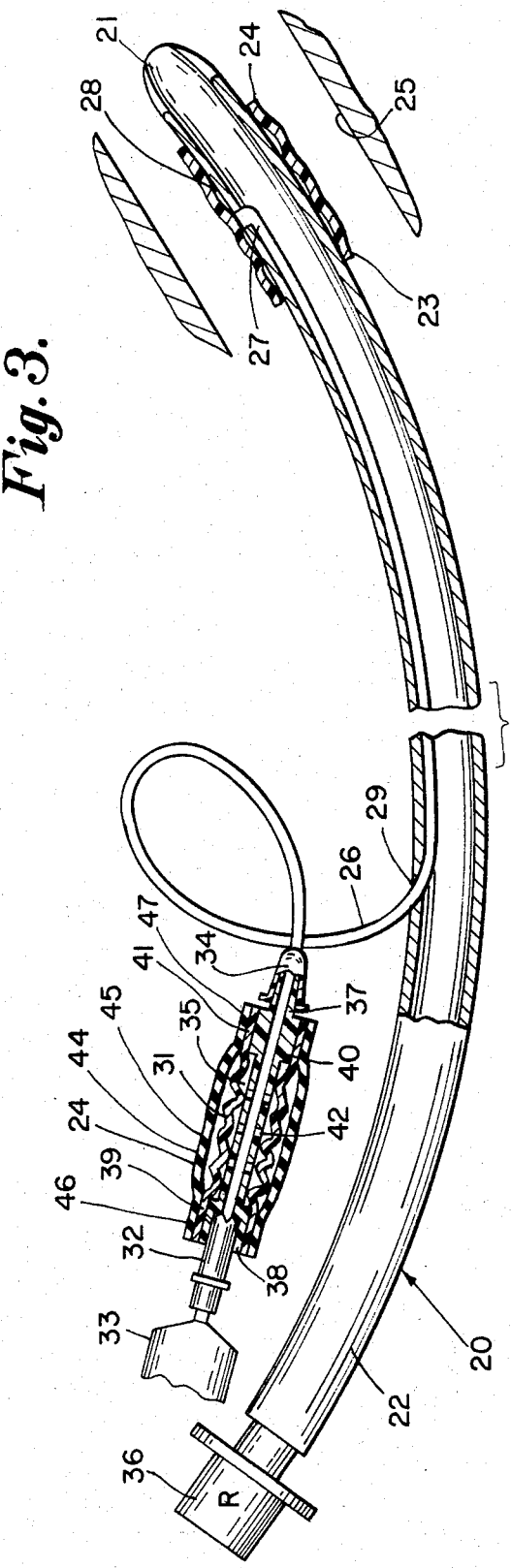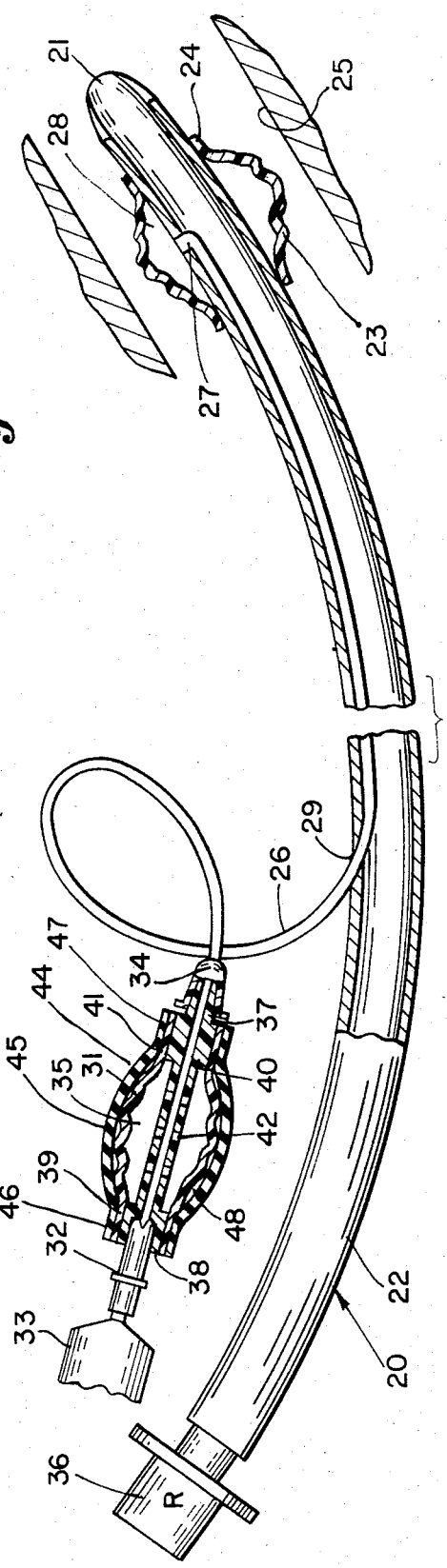

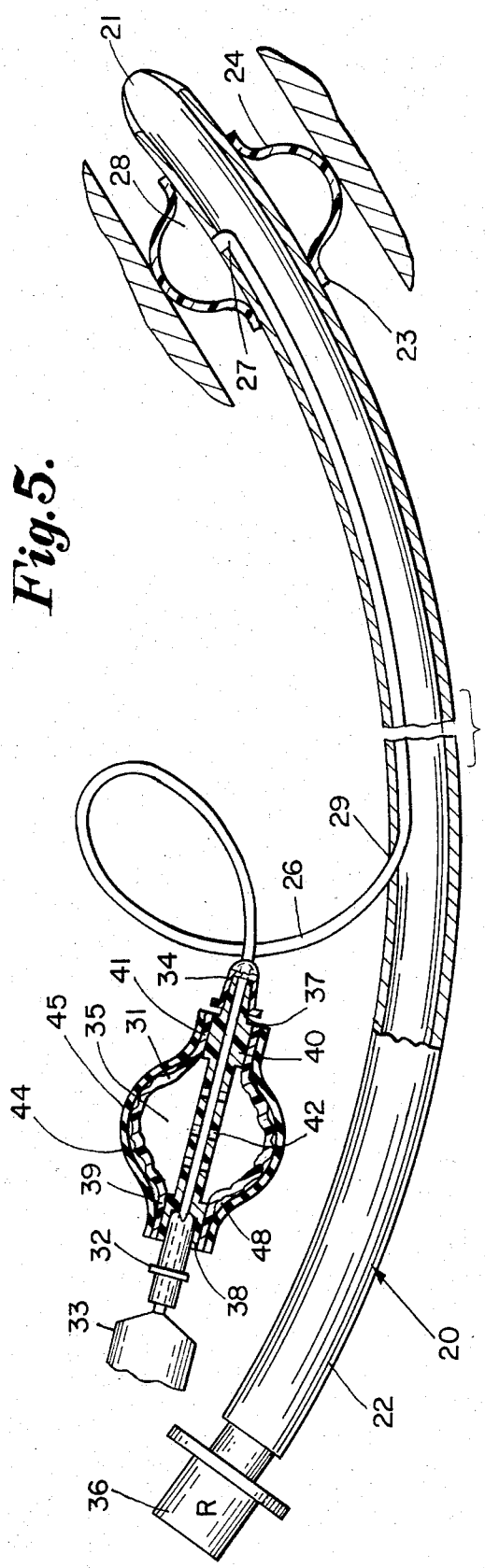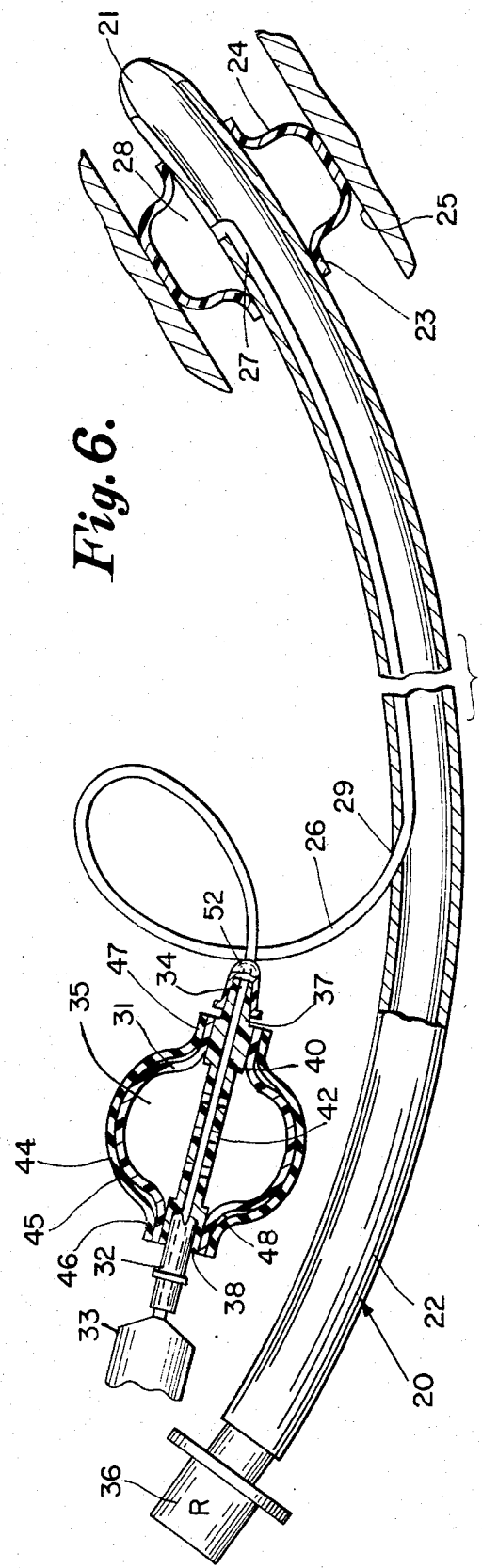

PRESSURE WARNING, INDICATING AND APPLYING MONITOR FOR CUFF TYPE INDWELLING DEVICES

BACKGROUND OF THE INVENTION

It has heretofore been proposed to provide indwelling devices, such as catheters, with an inflatable cuff of flexible material at the distal end inside the body, the cuff being inflatable from outside the body by an elongated tubule leading along the catheter to a one way valve and syringe type pump outside the body.

It has also been proposed to interpose in the tubule near the proximal end, between the valve and the cuff, an inflatable pilot balloon so that inflation of the pilot balloon indicates inflation of the cuff within the body.

Such an inflation indicating bulb is disclosed in U.S. Pat. Nos.

2,883,986 to DeLuca et al Apr. 28, 1959
3,543,751 to Sheffer of Dec. 1, 1970
3,810,474 to Cross of May 14, 1974
3,989,571 to Hardutuneian of Nov. 2, 1976
4,178,939 to Stephens of Dec. 18, 1979.

In addition to merely indicating inflation or deflation of the cuff by corresponding inflation or deflation of an exterior pilot balloon, there are patents which disclose means on the pilot balloon for indicating the amount of pressure of inflation.

In U.S. Pat. No. 3,407,817 to Galleher, Jr. of Oct. 29, 1968 a tubular coil unwinds as pressure on a finger bulb pump is exerted, the greater the unwinding the greater the pressure in the cuff.

U.S. Pat. No. 4,016,885 to Bruner of Apr. 12, 1977 discloses an inflatable cuff type catheter with a pressure indicating means in the form of an expansible chamber having an open ended spring wound therearound, expansion of the spring indicating gas pressure.

U.S. Pat. No. 4,018,231 to Wallace of Apr. 19, 1971 discloses a pilot balloon which is pre-stretched in deflated condition with spaced folds forming ridges and troughs to signal visually the non-inflated condition. The ridges expand radially to indicate inflation visually.

SUMMARY OF THE INVENTION

In this invention the inflatable cuff at the distal end of the indwelling device and the inflatable balloon at the proximal end of the tubule provided for cuff inflation are both formed of flexible, but non-resilient, non-stretchable thin material so that they each expand to full volume only.

Preferably, the inflatable pilot balloon has each opposite end sealed at a spaced distance apart around the tubule, or a tubule extension so that an opening in the tubule, or extension will admit air for inflation while the cuff is being inflated through the usual one way check valve by the usual syringe type pump.

Unlike the above mentioned pilot balloon devices of the prior art, however, the pilot balloon of this invention is what I call spherical shape in configuration, when inflated, with a short longitudinal axis and a relatively long diametrical axis.

In addition to not only visually indicate the amount of pressure in the cuff to warn of under inflation or over inflation and to apply resilient pressure in the event of loss of pressure, I provide a third balloon, of resilient, flexible, stretchable, material. The third balloon encloses the non-stretchable pilot balloon on the tubule, or tubule extension, but is not connected to the air in the tubule, so that it's exterior configuration depends on the configuration of the pilot balloon.

Thus, when no air pressure exists, the cuff, the pilot, and the pressure monitoring third balloon are all normally collapsed, the cuff and pilot being deflated. The opposite ends of the pressure monitoring third balloon are sealed to the tubule, or tubule extension at a spaced distance apart greater than the distance between the ends of the pilot balloon, but straddling the same so that the third balloon is elongated, to entirely encircle and enclose the pilot balloon, within its sealed chamber.

When the pilot balloon and cuff are expanded with air pressure so that the pilot balloon assumes a relatively small diameter shape, the pressure monitoring third balloon assumes an elongated generally cylindrical or sausage shape visually indicating that pressure is low in the cuff.

When the pilot balloon and cuff are further expanded with air pressure to cause the pilot balloon to form a drum shape of greater diameter, the pressure monitoring third balloon assumes an oval shape visually indicating that cuff pressure is medium.

If the pilot balloon expands to full diameter shape under air pressure to the cuff, the pressure monitoring third balloon assumes a spherical or globular shape visually indicating that cuff pressure is high.

Because the third balloon is of resilient, stretchable material, it continuously exerts inward pressure, of a predetermined amount, on the pilot balloon which in turn tends to maintain cuff pressure in the event of slight leakage or loss of cuff grip.

DESCRIPTION OF THE DRAWINGS

FIG. 1 is an exploded side elevational view of the parts of my new monitor device;

FIG. 2 is a similar view showing the parts thereof assembled, as the device can be used with any cuff type indwelling device;

FIG. 3 is a diagrammatic, side elevation of a cuff type indwelling device with the pressure monitoring device of the invention thereon, all balloons being collapsed;

FIG. 4 is a view similar in FIG. 1 showing low pressure in the cuff balloon and the third balloon so indicating by its small diameter, generally cylindrical shape;

FIG. 5 is a view similar to FIGS. 1 and 2 and showing medium pressure in the cuff balloon and the third balloon so indicating by its oval shape;

FIG. 6 is a view similar to FIGS. 1, 2, and 3 showing high pressure in the cuff balloon and the third balloon so indicating by its spherical shape.

DESCRIPTION OF A PREFERRED EMBODIMENT

Figure 7:
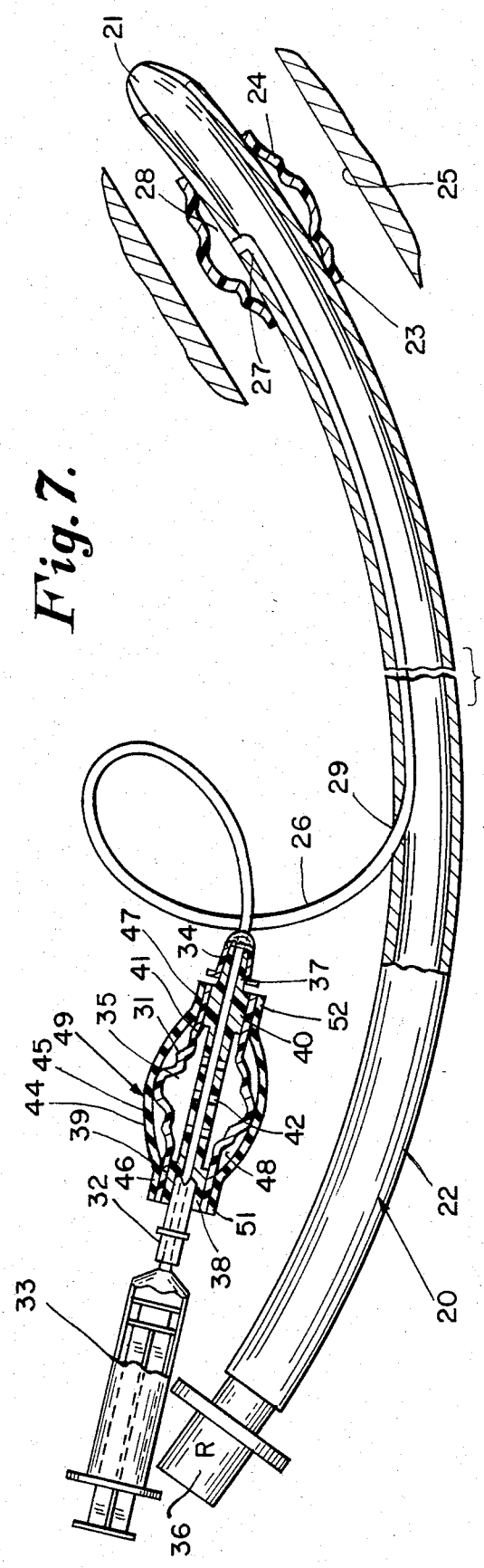
FIG. 7 is a view similar to FIGS. 1-4, but showing the pressure monitoring device of the invention as a separate article of commerce, applicable to any cuff type device.

A typical hollow, tubular, indwelling device 20, such as an endotracheal tube, is shown in the drawings, the tube 20 having a distal end 21 for insertion in a body cavity and a proximal end 22 projecting from the body cavity.

Conventionally, the tube 20 is provided with a normally collapsed, flexible, annular, expansible cuff 23 of thin membranous material 24 which is non-resilient and non-stretchable. The cuff 23 is annular, elongated and encircles the distal end 21 of the tube 20 so that when inflated, and expanded radially, it will affix the distal end 21 in the cavity 25 to avoid inadvertent dislodgment.

Conventionally also, a hollow tubule 26 of small diameter, has its distal end 27 in communication with the interior 28 of the cuff 23 and thence extends along the tube 20 to a point 29 whence it emerges for connection outside the body of the patient to a pilot balloon 31, a one way valve 32 and a source of air pressure such as the syringe type pump 33. The pilot balloon 31 is formed of the non-resilient-non-stretchable, flexible material 24. The proximal end 34 of the tubule 26 is connected to the interior chamber 35 in the pilot balloon 31 and in the above mentioned prior art patents the balloon is usually a bulge in the tubule with one end of the bulge leading to the valve and the other end of the bulge leading to the cuff. Thus, it indicates only inflation or deflation of the cuff.

In use the proximal end 22 of the tube 20 is connected to a respirator 36, the distal end 21 is inserted into the body cavity 25 and the pump 33 actuated to inflate the cuff while also inflating the pilot balloon 31 until the surgeon believes that cuff pressure is correct and not so great as to cause injury.

In this invention the pilot balloon 31 is not merely a bulge in the tubule, but instead includes a hollow tubular tubule extension 40 having one end 37 connected to the proximal end 34 of the tubule and the opposite end 38 connected to the one-way valve 32, or integral therewith. The non-stretchable, non-resilient expansible annular pilot balloon 31, when fully inflated, is of spherical shape with each opposite end 39 and 41 sealed around the tubule extension 40 and relatively closely spaced apart on each opposite side of the air apertures 42 which inflates the interior chamber 35 from the air in the tubule.

A pressure monitoring, or third balloon 44 is provided formed of resilient, stretchable flexible material 45 and having its opposite ends 46 and 47 sealed around the tubule extension 40 at a predetermined distance apart preferably greater than the distance between the ends 39 and 41 of the pilot balloon 31. The pressure monitoring balloon 31 is annular and elongated to entirely encircle and enclose the pilot balloon 31 in its sealed interior chamber 48, but chamber 48 is not connected to the air in tubule 26 and is sealed airtight therefrom.

In operation, the cuff 23, pilot balloon 31 and pressure monitoring, or third, balloon 44 are all normally collapsed when the distal end 21 of the indwelling device 20 is inserted into a body cavity such as 25 in the body of a patient as shown in FIG. 3.

In FIG. 4, the cuff 23 is shown partially inflated and the pilot balloon 31 is also shown partially inflated to assume a small diameter shape which in turn stretches the pressure monitoring balloon 44 into the generally cylindrical shape shown. This visually indicates to the surgeon not only the pressure in the cuff, but the generally cylindrical shape visually indicates that pressure is low, thus warning him that the cuff may become loose and fail to anchor the tube in the cavity.

In FIG. 5, the cuff 23 is shown with medium inflation and the pilot balloon 31 is correspondingly inflated into a shape of increased diameter thereby stretching the pressure monitoring balloon 44 into oval shape. The oval shape is an indication to the surgeon that pressure is just sufficient to firmly anchor the distal end of tube 20 in cavity 25 without injury to membranes, or the like.

In FIG. 6, the pilot balloon has become inflated to full radial shape thereby stretching the resilient pressure monitoring balloon 44 into substantially spherical shape which is a warning to the surgeon that there may be overpressure in the cuff 21 which may cause injury to the patient and perhaps should be reduced.

It will be noted that in the event of pressure leakage in the cuff, pilot or tubule during cuff application, the resilient balloon 44 applies continuous inward resilient pressure tending to compensate for leakage and maintain the cuff in place.

The embodiment of the invention, shown at 49 in FIGS. 1 and 7 is capable of being interposed into any cuff type indwelling device by being interposed between pump 33 and the proximal end 34 of tubule 26. The one way valve 32 may be integral with the tubule extension 40 or be a separate element, connected by suitable valve 32, tapered connectors or the like, all well known in the art such as at 51 and 52.

I claim:

1. In combination with a hollow tubular, indwelling device having distal and proximal ends; a normally collapsed, flexible, annular, expansible cuff encircling the tube proximate the distal end; a tubule having a distal end communicating with the interior of said cuff, thence extending along said device to a proximal end adapted to be connected to a source of air under pressure for inflating said cuff;

a normaly collapsed, annular pilot balloon, of non-resilient, non-stretchable flexible material having opposite ends sealed at a predetermined distance apart around said tubule proximate the proximal end thereof, said pilot balloon having an interior chamber connected by air apertures to the interior of said tubule for inflation thereby and, when fully expanded, being of short longitudinal axis, long radial axis, generally spherical shaped configuration;

and a normally collapsed annular pressure-monitoring balloon of resilient, stretchable, flexible, material, having opposite ends sealed at a predetermined distance apart around said tubule and entirely encircling and enclosing said pilot balloon, and forming an airtight sealed chamber therearound, said pressure monitoring balloon when expanded by contact of said pilot balloon progressively changing it's exterior shape to indicate changes in cuff pressure.

2. A device as specified in claim 1 wherein:
said inflatable cuff is of non-resilient, non-stretchable material.

3. A device as specified in claim 1 wherein:
said pressure monitoring balloon, upon progressive inflation of said cuff by said tubule, becomes successively elongated generally cylindrical in shape to indicate low pressure, elongated oval in shape to indicate medium pressure, and substantially spherical in shape to indicate high pressure.

4. In a cuff type indwelling device the combination of:
normally collapsed, inflatable cuff means, at the distal end of said device;
elongated tubule means, extending along said device, from said cuff means to a source of air pressure for inflating said cuff means from outside the body of a patient;
normally collapsed, inflatable pilot balloon means, of non-resilient, non-stretchable flexible material encircling said tubule means at a location outside said body, said tubule means being connected to said pilot balloon means by air apertures for inflation when said cuff means is inflated; and normally collapsed, elongated, resilient, stretchable balloon means, encircling said pilot balloon means, at said location, for assuming progressively different, recognizable, stretched, configuration as said pilot balloon is inflated to indicate different pressures in said cuff means.

5. A cuff type indwelling device as specified in claim 4 wherein:
said cuff means and said pilot balloon means both are formed of full volume non-stretchable, non-resilient, flexible material.

6. A cuff type indwelling device as specified in claim 4 wherein:
said pilot balloon means, when expanded, is relatively short axially and relatively long radially while said pressure monitoring balloon means, when expanded, is relatively long axially and relatively short radially.

7. A balloon type indwelling device of the type comprising:
an elongated, hollow, tubular, indwelling device, having an inflatable cuff balloon extending therearound, proximate the tip thereof which is inserted into a body cavity;
an inflatable pilot balloon adapted to remain outside the body to indicate inflation, a tube having air apertures connecting said cuff balloon with said pilot balloon and means for inflating both of said balloons simultaneously, characterized by;
said cuff balloon and said pilot balloon both being of non-resilient, non-stretchable, flexible material;
said pilot balloon being of substantially spherical configuration when fully inflated and;
said device including a pressure monitoring balloon of resilient, stretchable, flexible material, of greater length than the length of said pilot balloon and entirely enclosing the same, to form an airtight, sealed chamber therearound;
said pilot balloon and said pressure monitoring balloon, when deflated, indicating no pressure in said cuff balloon, when said pilot balloon assumes increased diameter to stretch said pressure monitoring balloon to elongated cylindrical shape, said elongated cylindrical shape indicating low pressure in said cuff balloon;
when said pilot balloon assumes greater diameter to stretch said pressure monitoring balloon to oval shape, said shape indicating medium cuff pressure in said cuff balloon; and when said pilot balloon assumes full diameter shape to stretch said pressure monitoring balloon to substantially spherical shape, indicating too much press in said cuff balloon.

8. Apparatus for monitoring the amount of pressure in the balloon cuff, at the distal end of an indwelling device, while inserted in a body cavity, said device having a tubule extending from the inflatable cuff along the device to a source of air pressure outside the body, said apparatus comprising:
a tubule extension having a nipple at one end for connection to a source of air under pressure, a one way valve at said end for preventing back flow out said end and having a nipple at the opposite end for connection to said tubule to inflate said cuff balloon;
an annular pilot balloon of non-stretchable material extending around said tubule extension and having an interior chamber connected by air apertures to the interior thereof for inflation thereby, said pilot balloon, when fully expanded being of generally spherical configuration;
and an annular pressure, monitoring balloon of stretchable resilient material extending around and enclosing, said pilot balloon on said extension and having an interior chamber which is airtight sealed relative to said pilot balloon, said pressure monitoring balloon being of greater axial length than said pilot balloon and assuming an elongated generally cylindrical shape when said cuff pressure is low, an oval shape when said cuff pressure is medium, and a spherical shape when said cuff pressure is high.

9. In combination with an indwelling device having an inflatable cuff at the distal end and a tubule adapted to extend outside the patient's body to inflate the cuff:
a tubule extension adapted to be connected between a source of air under pressure and the proximal end of said tubule, said extension including a one-way valve to prevent back flow;
a pilot balloon of non-stretchable material, adapted to be inflated when the cuff is inflated, said pilot balloon extending around said tubule extension and being inflatable by air apertures therein, said pilot balloon being of generally spherical shape when fully inflated;
and a pressure monitoring balloon of stretchable, resilient material, enclosing said pilot balloon in an airtight sealed chamber and extending therearound on said tubule extension, said pressure monitoring balloon progressively changing from elongated cylindrical, to oval, to spherical configuration as said cuff and pilot balloons are progressively expanded.

* * * * *